United States Patent [19]

Johnston et al.

[11] 4,127,383
[45] Nov. 28, 1978

[54] FOAMING WASTE TREATMENT COMPOSITION AND METHOD FOR TREATING NITROGENOUS WASTE MATERIAL THEREWITH

[75] Inventors: F. Bertram Johnston; Roland S. Grybek, both of Tampa, Fla.

[73] Assignee: Graham-White Sales Corporation, Salem, Va.

[21] Appl. No.: 805,515

[22] Filed: Jun. 10, 1977

[51] Int. Cl.$^2$ ............................. A61L 9/01; B01J 1/18
[52] U.S. Cl. ........................................ 422/5; 422/41; 71/3; 252/307; 252/353; 252/354; 252/355; 424/76
[58] Field of Search .............. 252/307; 21/55; 424/76; 71/3; 21/60.5 A

[56] References Cited

U.S. PATENT DOCUMENTS

| | | | |
|---|---|---|---|
| 1,485,333 | 2/1924 | Hurt | 21/55 X |
| 2,433,625 | 12/1947 | Raspet | 252/307 |
| 3,669,898 | 6/1972 | Butler | 252/307 |
| 3,713,404 | 1/1973 | Lavo et al. | 252/307 X |
| 3,762,875 | 10/1973 | Burmeister | 21/60.5 A |
| 3,978,208 | 8/1976 | Okadaa | 424/76 |
| 3,986,979 | 10/1976 | Moorer et al. | 252/354 X |
| 3,989,498 | 11/1976 | Cox | 71/3 |

Primary Examiner—Richard D. Lovering
Attorney, Agent, or Firm—Wilmer Mechlin

[57] ABSTRACT

A waste treatment composition and process wherein a salt of lignosulfonic acid and a foam-forming surfactant system are applied to nitrogenous waste material.

9 Claims, No Drawings

FOAMING WASTE TREATMENT COMPOSITION AND METHOD FOR TREATING NITROGENOUS WASTE MATERIAL THEREWITH

BACKGROUND OF THE INVENTION

1. Field of the Invention

This invention relates to the treatment of domestic sewage sludge, garbage, animal manures and similar nitrogenous waste material and the scrubbing of stack gases. More particularly this invention relates to a unique composition essentially consisting of a salt of a lignosulphonic acid and a foaming surfactant system and the use thereof in treating nitrogenous wastes. When applied in the form of a dried powder or as a solution, it serves the multiple function of odor control, containment of evolved gases, stabilization of amines and the proteinaceous components and the reduction of associated populations of noxious insects. The lignosulphonic acid-salt surfactant composition need merely be applied to the surface or intimately mixed with the organic debris. Even subsequent drying or admixture with soil as an organic additive, does not overcome this most desirable odor-free characteristic that has been imparted.

2. Description of the Prior Art

Treatment and disposal of primary domestic sewage sludge is an ever increasing problem. Outright incineration is costly and a source of atmospheric pollution. Open air drying gives off large volumes of malodorous gases. Such drying also encourages development of dense fly populations. It also requires large land areas, which is obviously undesirable. Artificial rapid drying is costly and produces difficult to control malodorous stack gases. Scrubbing of stack gases may even be required by the environmental authorities. The resultant sludge may contain high concentrations of pathogenic bacteria (e.g. samonella, clostridia, staphlococci, and pathogenic protozoa). Such sludge can usually be applied to agricultural soils only under the most stringent conditions.

Compounding the aforementioned problems is the fact that there is a tremendous volume of animal waste generated daily in the United States. It currently amounts to over 2 billion tons annually. Its high biochemical oxygen demand and the nutrient materials and pathogens contained therein, makes it a serious source of water pollution if disposed of in land runoffs. Large scale poultry and cattle farming creates even greater problems especially when urban development encroaches upon farmland areas. The development of insects and malodors is intolerable as urban development supercedes farmland. Fish kills, eutrophication of lakes, nitrate contamination of aquifers, dusts and off-flavors of surface waters are frequently associated with such animal husbandry.

SUMMARY OF THE INVENTION

Objectives

An object of this invention is to provide a unique waste treatment composition.

Another object is to provide a novel, simple process for the treatment of wastes.

Still another object is to provide a comosition for the treatment of wastes which is easily made from economic, readily available raw materials.

A further object is to provide a process for the treatment of wastes which utilizes an industrial waste by-product.

A still further object is to provide a composition which, simply when applied to waste material makes it relatively odor-free thereafter.

Another object is to provide a composition which, when applied to proteinaceous materials, stabilizes the amines and ammonia contained therein.

Other objects of the invention will in part be obvious and will in part appear hereinafter.

Broad Description of the Invention

In accord with the above objectives, a unique waste treatment composition has now been found. It comprises a salt of a lignosulphonic acid and a surfactant system.

The acid may be a by-product of the sulphite process of pulp paper manufacture. It may be the sodium, potassium, magnesium, ammonium or calcium salt of lignosulphonic acid. Its concentration range should be 15 to 85% by weight, dependent upon the physical makeup desired, i.e., solid or solution.

The surfactant may be an anionic surfactant such as an alkyl aryl sulfonate. Or it may be a non-ionic surfactant, such as an alkylphenoxy polyethoxy ethanol or a suitable combination thereof.

To provide foaming, it is preferred that an additional surfactant capable of generating foam be utilized. Such may be a sodium lauryl sulfate, coconut oil acid ester, a sulfated alkoxylated primary alcohol salt, a sulfated alkyl alcohol alkoxylate, an alkoxylated adduct of an alkyl aryl sulfonate alkanolamide, a salt of a sulfated polyglycol ether.

The froth or foam serves the dual function of (1) providing a blanket through which volatile gases generated in the decomposing mass must pass in an effort to escape into the atmosphere, and (2) furnishing extended many times repeated liquid-gas interfaces, thereby increasing the absorption and reactive capacity of the lignaceous material utilized of this invention.

In addition, a foam stabilizer, such as a cellulose gum, is preferred as a still further ingredient. One example is sodium carboxymethyl cellulose. Others are sodium alkyl sulfosuccinate, coconut oil fatty acid amine condensate, fatty acid amine condensate, hydroxyethyl cellulose and cellulose or other natural or synthetic gums. It is preferred that the foam stabilizer selected be one which does not contribute to the odor problem for extended periods of time. There are many which do not.

It is occasionally desirable to include a humectant to absorb moisture from the air to aid in keeping the foam bubbles intact. Glycerine and ethylene glycol are useful examples. Additionally, a small amount of formalin is incorporated to minimize mold development in the formula concentrate, which contains as normal ingredients from the commercial lignin component appreciable quantities of wood sugars.

The invention accordingly comprises the several steps and the relation of one or more of such steps with respect to each of the others, and the composition possessing the features, properties and the relation of components which are exemplified in the following detailed disclosure and the scope of the invention will be indicated in the claims.

DETAILED DESCRIPTION OF THE PREFERRED EMBODIMENTS

For a fuller understanding of the nature and objects of the invention, references should be had to the following detailed examples:

EXAMPLE I

The following ingredients are admixed:

| | |
|---|---|
| Calcium Lignosulfonic Acid | 27.4% by weight |
| Ammoniacal Nitrogen | 0.3% |
| Formalin | 0.8% |
| Ethylene Glycol | 0.2% |
| Sodium Carboxymethyl Cellulose | 0.3% |
| Dioctyl Sodium Sulfosuccinate | 1.0 |
| Water | 70.0% |
| | 100.0% |

The above composition is diluted to a 1% by weight solution for spray application. When sprayed to a wet surface condition upon domestic sewage sludge, no odor will be detected. The usual housefly larvae infection will not appear nor will there be ovi-depositing of noxious insects. Apparently the composition chemically reacts with the volatile odor bodies and nitrogenous components to form a stabilized complex of very low volatility. Such is of little attraction to insects.

EXAMPLE II

The following composition is admixed as a dry powder:

| | |
|---|---|
| Ammonium lignosulfonic acid (Dry) | 85.0% |
| Sodium Carboxymethyl Cellulose (Dry) | 5.0% |
| Sodium Bentonite | 5.0% |
| Sodium Lauryl Sulfate | 5.0% |
| | 100.0% |

Eight pounds of the above composition are dispersed in 100 gallons of water to provide an approximately 1% solution for spraying.

When sprayed as a solution on a garbage dump, the odor will be substantially reduced. It will also be noted that there will be a minimum of housefly larvae infestation. It will also discourage ovipositing of noxious insects.

EXAMPLE III

Soil mixtures of 50 parts by weight sandy loam and 50 parts sewage sludge compost prepared as in Example I and 90 parts sandy loam and 10 parts compost prepared in accord with Example I are prepared and admixed with a 6/6/6 standard soil fertilizer. When subjected to lysimeter tests the following results should appear:

| | | Immediately after 40" water added | | 15 days after 40" water added | |
|---|---|---|---|---|---|
| Ion | Orig. Meq. | Sandy Loam Only | Loam & Compost 50:50 | Loam & Compost 90:10 | Loam & Compost 50:50 | Loam & Compost 90:10 |
| Potassium | 40 | 4 | 20 | 10 | 30 | 22 |
| Calcium | 40 | 15 | 30 | 25 | 50* | 35 |
| Magnesium | 20 | 8 | 15 | 15 | 20 | 15 |
| Phosphate | 40 | 7 | 30 | 20 | 35 | 30 |

*probably due to the release of available calcium from the calcareous components of the particular soil utilized.

From the above results it should be evident that both the 50:50 and 90:10 mixtures retain more milliequivalents of potassium, calcium, magnesium and phosphate than the sandy loam without any compost therein. Thus, it can be concluded that the composition of this invention has greater retention for a particular desired ion in solution for a longer period of time than without.

EXAMPLE IV

A series of tests are run using the sewage sludge compound of Example I to determine the retention of urea. Parts by weight of urea is used in all instances. A 15" test depth of soil is used.

The following lysimeter values are obtained:

| | PER CENT RETENTION | | | |
|---|---|---|---|---|
| Application of Water | Immediate | | After 20 days In Soil at 70° F | |
| Percolation (equiv. inches) | 20" | 40" | 20" | 40" |
| Urea alone | 5% | 0% | 10% | 6% |
| The 50:50 Compost of Ex. I | 70% | 62% | 85% | 80% |
| A 50:50 Compost but without the lignosulphonic acid | 30% | 20% | 35% | 25% |

It should be evident that when the compost used is one pretreated using the composition of this invention, there is better retention of urea.

EXAMPLE V

When the soil compositions of Example III are utilized to cultivate various plants as indicated below, the following yields are obtained:

| | Tomatoes | Corn | Pole Beans |
|---|---|---|---|
| Yield | | | |
| Control (no compost) | 100 | 100 | 100 |
| 50:50 Compost of Ex. III | 125 | 115 | 130 |
| 90:10 Compost of Ex. III | 125 | 115 | 120 |
| Quality | | | |
| Control (no compost) | Average | Poor | Average |
| 50:50 Compost of Ex. III | Good | Tender | Good taste |
| 90:10 Compost of Ex. III | Good | Tender | Good Taste |

EXAMPLE VI

The spray solution of Example I is sprayed onto chicken manure. The measure of its effectiveness will be as follows:

| % Content (dried to 30% moisture) | Nitrogen | Phosphate | Potassium | Sulfur |
|---|---|---|---|---|
| Chicken Manure (fresh) | 1.8 | 1.8 | 1.0 | 0.1 |
| 2 Weeks Untreated* | 1.6 | 1.7 | 1.0 | 0.0 |
| 6 Weeks Untreated* | 0.7 | 1.0 | 0.5 | 0.0 |
| 6 Weeks Treated** | 2.0 | 1.7 | 0.9 | 0.1 |

*Exposed to normal outdoor weathering (composting) conditions.
**Increase in nitrogen due to microbial activity.

It should be evident that this invention improves the nitrogen, phosphate, potassium and sulfur content of chicken manure thereby making it a long lasting fertilizer.

EXAMPLE VII

When the spray solution of Example I is used to determine discouragement of ovipositing of houseflies on chicken manure, the following test data will be obtained, based upon estimated insects per square foot:

|  | In Air Over Pile | On Manure |
| --- | --- | --- |
| Untreated | 25 | 40 |
| Immediately after spraying | 30 | 5 |
| 1 Hour after spraying | 5 | 0 |
| 1 Day after spraying | 1-2 | 0 |
| 6 Days after spraying | 5 | 5* |

*Fresh deposits by chickens are involved.

Tests of spraying on livestock indicate discouragement from lighting of houseflies and face flies and of flea infestation.

Again, it should be evident that ovipositing of houseflies is discouraged.

The lignosulphonic acid component may be readily obtained from an economical industrial by-product in the sulfite process of pulp-paper manufacture. This by-product in fact, until now, currently finds very limited commercial utility. Its disposal until now, has constituted a major problem.

This lignaceous component, by virtue of its high chemical activity reacts with volatile and unstable ingredients, including amines, sulfides and certain aromatics to form low volatile, highly stable complexes. Applied in the amounts recommended, it conserves the nitrogenous and sulfurous components of the usual waste products without appreciably interferring with the usual enzymatic and microbiological degradation that occurs in nature.

The lignin sulfonic acid component also acts as a flocculating agent, so that composting may even be commenced during conditions of high moisture content of sewage sludge and manures.

Another feature of this invention is that now domestic sewage sludge and manures treated with the formula of this invention are readily handleable. They can be conveniently managed by conventional drying and composting procedures. Indeed, from an environmental standpoint, composting is highly preferable to disposal by burning. It is, in fact, more economical. Additionally, it serves the best interest of conservation. Furthermore, the objectionable odors of conventional aerobic sludge decomposition are almost entirely eliminated by application of the formula of this invention. And, upon completion of the composting process, the dry "stabilized" end product no longer generates malodors upon being re-wetted.

Use of the formula of this invention also substantially shortens the time required for "stabilizing" or completion of composting of sludges and manures.

Sludge and manures, as is well known, contain small but appreciable percentages of agriculturally useful components; mainly, potassium, nitrogen and phosphorus. These are mostly in the form of organic compounds which, by the addition of the composition of this invention can be rendered relatively non-leachable. Thus, when added to the soil, they are in a form readily available for plant nutrition but are not leached by rain or irrigation.

Such sludge and manures benefit the soil by addition of cellulosic organic matter, with resultant mulching action, improvement of soil tilth, porosity and water retention. Reactive ingredients of such composts assist in normal weathering of soil minerals to provide nutrients to the soil solution.

An important ancillary benefit is the discovery that composts prepared by incorporation of the composition of this invention, whe intimately mixed with commercial fertilizers, provide improved retention in the soil and also contribute to their efficiency. Accordingly, the amount of commercial fertilizer which must ordinarily be applied to soil for a given area may be reduced, particularly in sandy soils.

Another important feature of this invention is its capability of conserving urea when added as a source of nitrogen to ordinary components.

The composition of the invention is safe for use around animals and poultry. With an almost neutral pH, it can be sprayed onto metal implements, machinery or concrete without damage.

It will thus be seen that the objects set forth above, among those made apparent from the preceding description, are efficiently attained and, since certain changes may be made in carrying out the above process and in the composition set forth without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention, which, as a matter of language, might be said to fall therebetween.

Now that the invention has been described,

What is claimed is:

1. A foaming waste treatment composition for stabilization of amine and the proteinaceous components thereof comprising about 15 to 85% by weight of a salt of a lignosulphonic acid and about 1 to 5% by weight of a mixture of surfactant of a member selected from the group consisting of alkyl aryl sulfonate and alkylphenoxy polyethoxy ethanol and a foam-generating member selected from the group consisting of sodium lauryl sulfate, coconut oil acid ester, a sulfated alkoxylated primary alcohol salt, a sulfated alkyl alcohol alkoxylate, alkoxylated adduct of an alkyl aryl sulfonate alkanolamide, salt of a sulfated polyglycol ether.

2. The waste treatment composition of claim 1 further including a foam stabilizer selected from the group consisting of sodium carboxymethyl cellulose, sodium alkyl sulfosuccinate, fatty acid amine condensate, hydroxyethyl cellulose and cellulose.

3. The waste treatment composition of claim 2 further including a humectant selected from the group consisting of glycerine and ethylene glycol.

4. The waste treatment composition of claim 2 wherein the salt is calcium lignosulfonic acid and the surfactant mixtures includes dioctyl sodium sulfosuccinate.

5. The waste treatment composition of claim 2 in liquid form wherein the salt is 27.4% by weight and the surfactant mixture is 1.0% by weight and the balance consists essentially of water.

6. The waste treatment composition of claim 2 in dry form wherein the salt mixture includes ammonium lignosulfonic acid and the surfactant is sodium lauryl sulfate.

7. A method for treating nitrogenous waste material comprising spraying a foamable dilute solution of the composition of claim 2 onto the surface of said waste material.

8. The method of claim 7 wherein said waste material comprises sewage sludge.

9. The method of claim 7 wherein said waste material comprises animal wastes.

* * * * *

UNITED STATES PATENT AND TRADEMARK OFFICE
CERTIFICATE OF CORRECTION

PATENT NO. : 4,127,383
DATED : November 28, 1978
INVENTOR(S) : F. Bertram Johnston and Roland S. Grybek It is certified that error appears in the above–identified patent and that said Letters Patent are hereby corrected as shown below:

Delete "Assignee: Graham-White Sales Corporation, Salem, Va.";

Attorney, Agent or Firm, delete "Wilmer Mechlin" and insert "Stein & Frijouf; P. A.";

Column 1, line 66, delete "cosmosition" and insert --composition--;

Column 5, line 67, delete "whe" and insert --when--.

Signed and Sealed this

First Day of May 1979

[SEAL]

Attest:

RUTH C. MASON
*Attesting Officer*

DONALD W. BANNER
*Commissioner of Patents and Trademarks*